United States Patent [19]

Umezawa et al.

[11] 4,420,473

[45] Dec. 13, 1983

[54] ANTIBIOTIC, MF266 SUBSTANCE AND PRODUCTION THEREOF

[75] Inventors: Hamao Umezawa; Tomio Takeuchi; Masa Hamada, all of Tokyo; Shinichi Kondo, Yokohama; Kiyoto Ishii, Tokyo, all of Japan

[73] Assignee: Zaidan Hojin Biseibutsu Kagaku Kenkyu Kai, Tokyo, Japan

[21] Appl. No.: 296,923

[22] Filed: Aug. 27, 1981

[30] Foreign Application Priority Data

Sep. 12, 1980 [JP] Japan .................................. 55-126087

[51] Int. Cl.$^3$ ......................... A61K 35/00; C12P 1/06
[52] U.S. Cl. ..................................... 424/118; 435/169
[58] Field of Search .......................... 424/118; 435/169

[56] References Cited

U.S. PATENT DOCUMENTS

| | | | |
|---|---|---|---|
| 3,183,157 | 5/1965 | Bhuyaw et al. | 424/120 |
| 3,590,028 | 6/1971 | Arcamone et al. | 424/180 |
| 3,997,662 | 12/1976 | Pinnert et al. | 424/119 |

OTHER PUBLICATIONS

Wiley et al., J. Am. Chem. Soc. 99 (2): 542–547 (1977).
Bvazhninova et al., Antibiotiki 11: 763–767 (1966).

*Primary Examiner*—Jerome D. Goldberg
*Attorney, Agent, or Firm*—David M. Morse

[57] ABSTRACT

New antibiotic designated MF266 substance is now obtained from fermentaton of a new microorganism Streptomyces MF266-g4 (desposited under FERM-P 5401 or ATCC 31910). This new substance is useful as antibacterial agent and/or an antitumor agent for the inhibition of experimental animal tumors.

5 Claims, 2 Drawing Figures

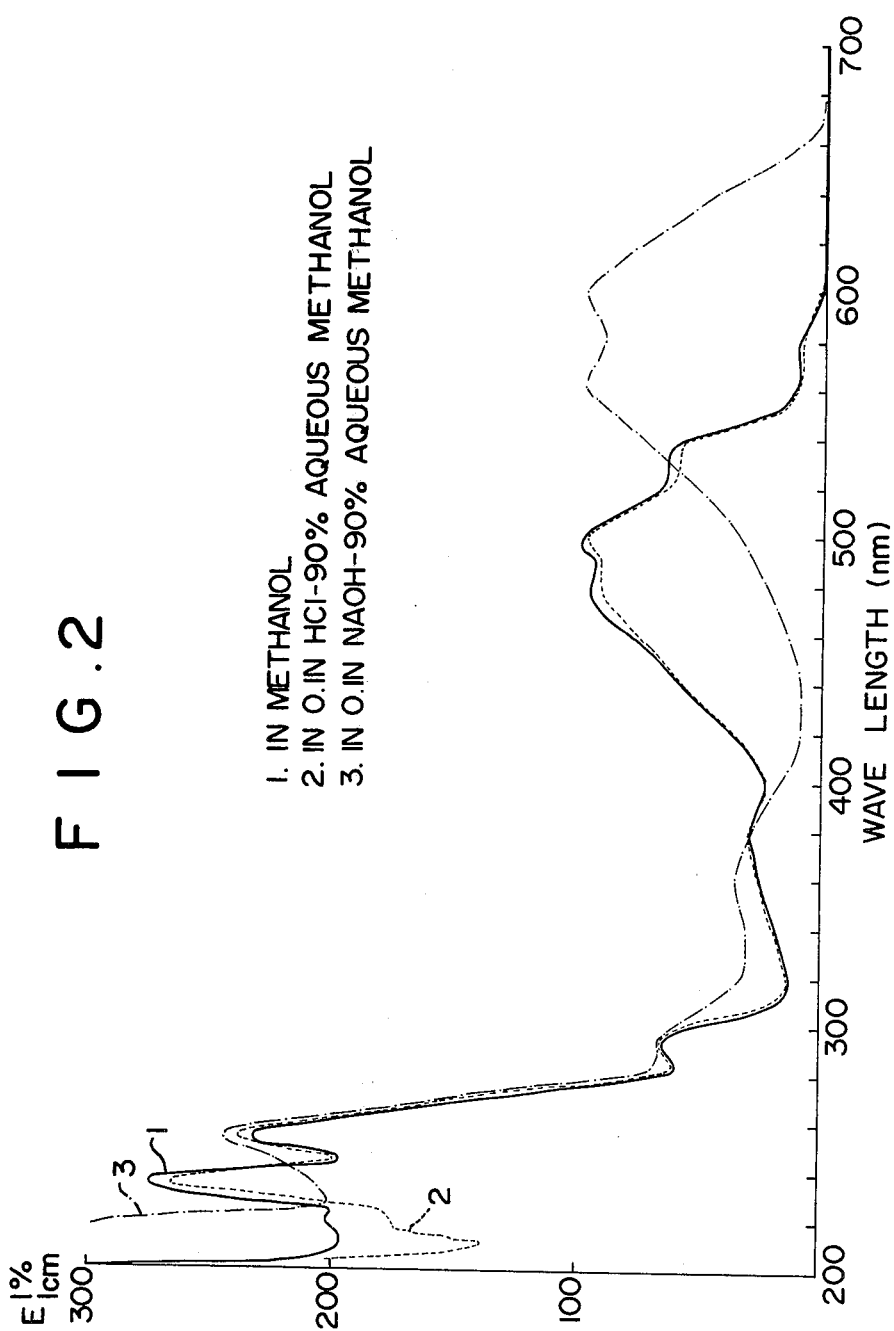

ANTIBIOTIC, MF266 SUBSTANCE AND PRODUCTION THEREOF

SUMMARY OF THE INVENTION

This invention relates to a new antibiotic designated MF266 substance which is obtained by fermentation of a new microorganism of the genus Streptomyces, which is of anthracycline group antibiotics and which exhibits a high activity inhibitory to the growth of gram-positive bacteria and the growth of mouse leukemia L-1210 cell. This invention also relates to a process for the production of the MF266 substance. This invention further relates to the recovery and purification of the MF266 substance and its use for pharmaceutical purposes.

BACKGROUND OF THE INVENTION

There are known many antibiotics which are produced by microorganisms of the genus Streptomyces and which are useful as antibacterial agent and/or as an antitumor agent for the inhibition of experimental animal tumors. In an attempt to obtain further new antibiotics, we collect various soil samples, isolate microorganisms from soil samples and investigate metabolic products as produced by aerobic cultivation of the isolated microorganisms. We isolated a new microorganism from a soil sample collected at Nishi-shinagawa, Shinagawa-ku, Tokyo, Japan, and we have designated this new isolated microorganisms as MF266-g4 strain. This strain has been confirmed to belong to the genus Streptomyces. We have succeeded to cultivate the MF266-g4 strain, produce and accumulate a new substance designated as MF266 substance in the culture of said strain and isolate the new substance from the culture.

We have now found that the isolated new substance, MF266 substance strongly inhibits the growth of various gram-positive bacteria and also inhibits effectively the growth of mouse leukemia L-1210 cell and is a new antibiotic.

DETAILED DESCRIPTION OF THE INVENTION

According to this invention, therefore, there is provided a new antibiotic, MF266 substance having the following properties.

The MF266 substance is an amphoteric compound of which the hydrochloride is in the form of a red-colored amorphous powder decomposing at 178°–180° C. and showing a specific optical rotation $[\alpha]_D^{25} = +370°$ (c 0.1, methanol). The hydrochloride gives an elemental analysis: C 49.00%, H 6.56%, N 3.39%, O 28.58%, Cl 7.17%. Its molecular formula and molecular weight are not yet decided. However, it is presumed that the MF266 substance has a molecular weight in the range of 1200 to 1300 from mass spectrometry of its methyl ester. The MF266 substance hydrochloride gives an infrared adsorption spectrum as shown in FIG. 1 of the attached drawings when pelleted in potassium bromide, and it gives an ultraviolet absorption spectrum as shown in FIG. 2 of the attached drawings. The MF266 substance hydrochloride in solution in methanol gives absorption maxima at 220, 235, 254, 290, 380, 475, 496, 535 and 575 nm with $E_{1\ cm}^{1\%}$ values of 208, 276, 232, 64, 28, 96, 100, 64 and 14, respectively. Further, the hydrochloride in solution in 0.1 N hydrogen chloride in 90% aqueous methanol gives absorption maxima at 220 (shoulder), 235, 254, 290, 380, 480, 497, 535 and 570 nm with $E_{1\ cm}^{1\%}$ values of 188, 264, 241, 64, 28, 92, 100, 60 and 14, respectively. The hydrochloride in 0.1 N sodium hydroxide in 90% aqueous methanol shows absorption maxima at 213, 253, 292, 360, 560 and 597 nm with $E_{1\ cm}^{1\%}$ values of 688, 247, 48, 36, 100 and 100, respectively.

The MF266 substance hydrochloride is soluble in water, methanol, dimethylsulfoxide and pyridine but sparingly soluble in such organic solvents as chloroform, acetone, benzene, and ethyl acetate, and it gives a single spot at Rf 0.27 in a thin layer chromatography on silica gel developed with chloroform-methanol-10% aqueous ammonium acetate (20:15:1 by volume); a single spot at Rf 0.06 in the same silica gel thin layer chromatography developed with chloroform-methanol (1:1 by volume); and a single spot at Rf 0.10 in the same silica gel thin layer chromatography developed with chloroform-methanol-acetic acid (20:5:1 by volume) as the eluent.

In view of the above-mentioned properties, it is confirmed that the MF266 substance is a new antibiotic of anthracycline type which is clearly distinguishable from the known antibiotics.

REFERRING TO THE ATTACHED DRAWINGS

FIG. 2 shows curves of the ultraviolet absorption spectrum of the MF266 substance hydrochloride when determined in methanol; in 0.1 N hydrogen chloride in 90% aqueous methanol; and in 0.1 N sodium hydroxide in 90% aqueous methanol, respectively.

Figure 1:
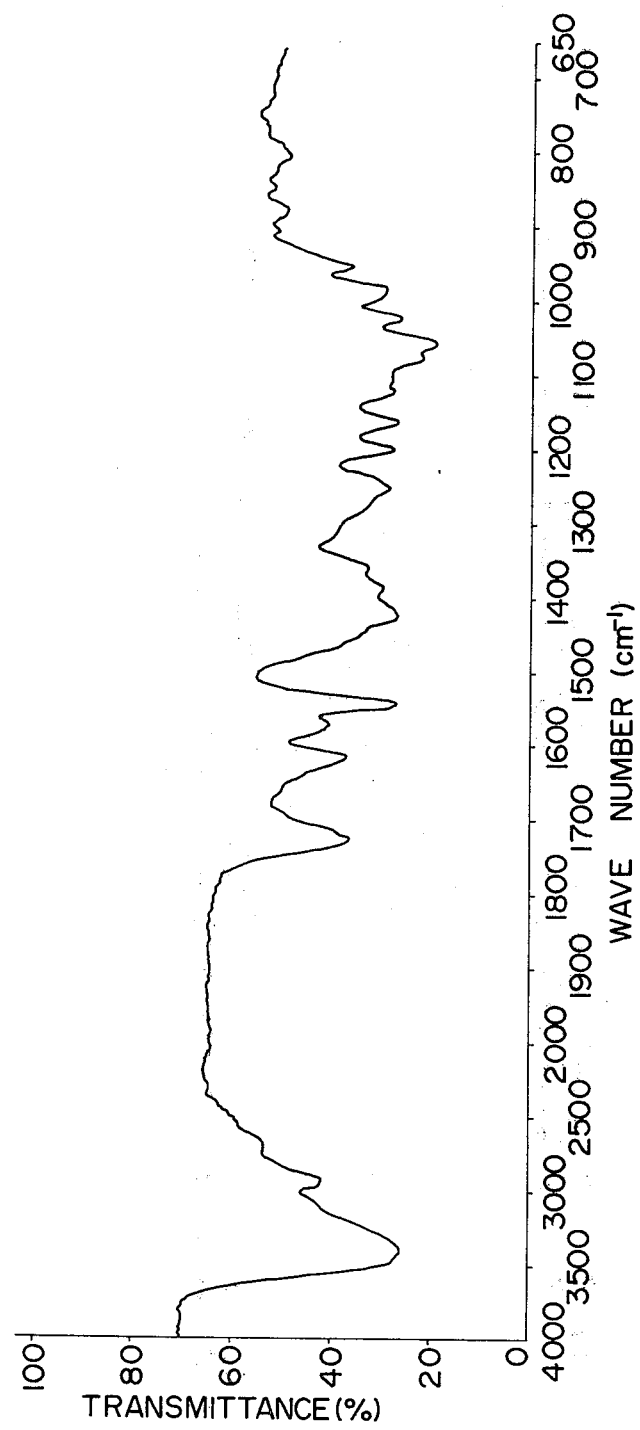
FIG. 1 shows a curve of the infrared absorption spectrum of the MF266 substance hydrochloride pelleted in potassium bromide.

The antibacterial spectrum of the MF266 substance hydrochloride is shown in Table 1 below, where the minimum inhibitory concentrations (mcg/ml) of said substance to various bacteria have been determined on nutrient agar plates as incubated at 37° C. for 17 hours.

The therapeutic effect of the MF266 substance hydrochloride against mouse leukemia L-1210 cell is shown in Table 2 below, where the rate (%) of survival was estimated by inoculating leukemia L-1210 cells into mice and then immediately intraperitoneally injecting the MF266 substance hydrochloride into the tumor-bearing mice once daily for 10 days to give remarkably favorable effect on the rate of survival of the treated mice.

TABLE 1

| Test organisms | MIC. (mcg/ml) |
| --- | --- |
| Staphylococcus aureus 209P | 1.56 |
| Staphylococcus aureus Smith | 6.25 |
| Micrococcus flavus FDA 16 | 3.13 |
| Micrococcus lysodeikticus IFO 3333 | 3.13 |
| Sarcina lutea PCI 1001 | 1.56 |
| Bacillus anthracis | <0.78 |
| Bacillus subtillis NRRL B-558 | 1.56 |
| Bacillus subtillis PCI 219 | 1.56 |
| Bacillus cereus ATCC 10702 | 1.56 |
| Corynebacterium bovis 1810 | 6.25 |
| Mycobacterium smegmatis ATCC 607 | 25 |
| Escherichia coli NIHJ | >100 |
| Escherichia coli K-12 | >100 |
| Shigella dysenteriae JS 11910 | >100 |
| Shigella flexneri 4b JS 11811 | 50 |
| Shigella sonnei JS 11746 | >100 |
| Salmonella typhi T-63 | >100 |
| Salmonella enteritidis 1891 | >100 |
| Proteus vulgaris OX 19 | >100 |
| Proteus mirabilis | >100 |

TABLE 1-continued

| Test organisms | MIC. (mcg/ml) |
|---|---|
| Proteus rettgeri GN 311 | >100 |
| Proteus rettgeri GN 466 | >100 |
| Serratia marcescens | >100 |
| Pseudomonas aeruginosa A3 | >100 |
| Klebsiella pneumoniae PCI 602 | 100 |
| Candida albicans 3147 | >100 |

TABLE 2

| Dosage (mcg/mouse/day) | Rate of survival (%)* |
|---|---|
| 50 | 177 |
| 25 | 139 |
| 12.5 | 127 |
| 6.25 | 120 |
| 3.13 | 114 |

In Table 2, the rate of survival (%) is calculated by the following equation:

$$\frac{\text{Average number of surviving days of treated mice}}{\text{Average number of surviving days of untreated mice}} \times 100$$

The results of Table 2 above for the therapeutic effects of the MF266 substance against leukemia L-1210 in mice were estimated by inoculating leukemia L-1210 cells ($10^5$ cells/mouse) intraperitoneally into mice of CDF 1 strain (weighing 19–22 g), and immediately after the tumor inoculation, injecting intraperitoneally the MF266 substance hydrochloride at dosages indicated in the table once daily for successive 10 days. The leukemic mice were used in groups each of four mice for each dosage. The intraperitoneal injection of the MF266 substance was found to exert highly favorable effects on improvement of the rate of survival of the L-1210-inoculated mice, as the rate (%) greater than 125 are generally considered significant.

Acute toxicity of the MF266 substance hydrochloride was estimated by intravenous injection in mice, when this hydrochloride exhibited an LD50 value of 50 to 100 mg/kg. It is also found that the MF266 substance hydrochloride is of less toxicity to heart, as compared to other known antibiotics of anthracycline type.

According to this invention, the MF266 substance is obtained in the free base form or in the form of an acid-addition salt thereof, either in a pure form or in a crude state or as a solution or as a purified or crude solid. For higher stability, the MF266 substance may preferably be recovered in the form of its pharmaceutically acceptable acid-addition salt as obtained in such a manner that the free base form of the MF266 substance is reacted with a pharmaceutically acceptable acid, including such inorganic acid as hydrochloric, hydrobromic, sulfuric, phosphoric and nitric acids and also such organic acid as acetic, malic, citric, ascorbic and methanesulfonic acids and so on. The MF266 substance of this invention may also be in the form of its pharmaceutically acceptable ester such as methyl and ethyl esters.

According to this invention, there is also provided a pharmaceutical composition, useful as antibacterial agent, comprising as the active ingredient an antibacterially effective amount of the MF266 substance of this invention or a pharmaceutically acceptable acid-addition salt or ester thereof, in combination with a pharmaceutically acceptable carrier for the active ingredient.

It will be appreciated that the actual preferred amounts of the MF266 substance used will vary according to the particular compound being used, the particular composition formulated, the mode of application and the particular situs and organism being treated. Many factors that modify the action of the drug will be taken into account by the skilled in the art, for example, age, body weight, sex, diet, time of administration, route of administration, rate of excretion, drug combinations, reaction sensitivities and severity of the disease. Optimal application rates for a given set of conditions can be ascertained by the skilled in the art using conventional dosage determination tests in view of the above guidelines.

According to a further aspect of this invention, there is provided a process for the production of the MF266 substance, which comprises cultivating an MF266 substance-producing strain of the genus Streptomyces under aerobic conditions in a culture medium containing assimilable carbon and nitrogen sources to produce and accumulate the MF266 substance in the culture, and recovering the MF266 substance from the culture.

As an example of the above MF266 substance-producing strain, there may be mentioned a strain of actinomycetes, designated as MF266-g4 strain, which was isolated from a soil sample collected in January of 1976 at Nishi-shinagawa, Shinagawa-ku, Tokyo. This strain has the following microbiological properties.

MICROBIOLOGICAL PROPERTIES OF THE MF266-g4 STRAIN

1. Microscopical morphology

MF266-g4 strain has branched substrate mycelia, from which aerial hyphae develop either in the form of open spirals or in the form of hook or in rectiflexifile form depending on the culture medium employed. No whirl-formation is observed. Matured spore chains usually bear more than 10 conidal spores. Spores are measuring about 0.6–0.8 by 0.8–1.2 microns in size and have smooth surface.

2. Characteristics of the growth on various culture media

The designation of colors in brackets mentioned below follows the color standard given in the "Color Harmony Mannual" published by Container Corporation of America.

(1) On sucrose-nitrate agar (incubated at 27° C.)

The colorless growth develops aerial hyphae of pinkish white to light brownish spray [5 cb] color. No soluble pigment is observed.

(2) On glucose-asparagine agar (incubated at 27° C.)

The growth is colored pale yellow to pale yellowish brown and develops no aerial hyphae. No soluble pigment is observed.

(3) On glycerol-asparagine agar (ISP-medium 5, incubated at 27° C.)

The growth is colored pale yellowish brown [2 gc, Bamboo] to light reddish orange [5 ia, Brite Peach to 5 lc, Copper] to dull orange [5 le, Rust Tan] and bears thin aerial hyphae of white to pale pink tinge. Soluble pigment is faintly tinged with yellow.

(4) On inorganic salts-starch agar (ISP-medium 4, incubated at 27° C.)

The growth is colored pale yellow [2 gc, Bamboo] to pale yellowish brown [2 ie, Lt Mustard Tan] and develops aerial hyphae of pinkish gray [5 ge, Rosewood] to light brownish gray [5 dc, Pussywillow Gray] color. Soluble pigment is faintly tinged with brown.

(5) On tyrosine agar (ISP-medium 7, incubated at 27° C.)

The growth is colored pale yellowish brown [2 gc, Bamboo to 2 ie, Lt Mustard Tan] to pink [4 gc, Nude Tan to 5 gc, Peach Tan] and develops aerial hyphae of pinkish white [5 ba, Shell Pink] to pinkish gray [5 ge, Rosewood] color. Soluble pigment is faintly tinged with yellow.

(6) On nutrient agar (incubated at 27° C.)

The growth is grayish yellow brown [4 pl, Dk Spice Brown] colored, without developing aerial hyphae. Soluble pigment is colored brown.

(7) On yeast extract-malt extract agar (ISP-medium 2, incubated at 27° C.)

The growth is colored pale yellowish brown [2 le, Mustard to 2 ie, Lt Mustard Tan] to pale reddish orange [5 ie, Copper Tan] and develops aerial hyphae of white to pinkish gray [5 ge, Rosewood] color. Soluble pigment is faintly tinged with yellowish brown.

(8) On oatmeal agar (ISP-medium 3, incubated at 27° C.)

The growth is colored pale yellow to pale yellowish brown [2 gc, Bamboo to 3 le, Cinnamon] and develops aerial hyphae of pinkish white to light brownish gray [5 ec, Dusty Peach to 5 ge, Rosewood] color. Soluble pigment is faintly tinged with yellow.

(9) On glycerol-nitrate agar (incubated at 27° C.)

The growth is colored pale yellowish brown [2 gc, Bamboo] to pale reddish brown [5 gc, Peach Tan] and develops aerial hyphae of pale pink [5 cb, to 5 ba, Shell Pink] color. Soluble pigment is faintly tinged with yellow.

(10) On starch agar (incubated at 27° C.)

The growth is colored pink [5 ic, Lt Persimmon] to pale reddish orange [5 le, Rust Tan] and develops aerial hyphae of pale pink [5 ec, Dusty Peach] to light gray [3 fe, Silver Gray] color. Soluble pigment is faintly tinged with pale red.

(11) On calcium malate agar (incubated at 27° C.)

The colorless to pale yellow colored growth develops aerial hyphae of pinkish gray to light brownish gray [5 ge, Rosewood to 5 ec, Dusty Peach] color. Soluble pigment is faintly tinged with pink.

(12) On cellulose (incubated at 27° C.)

The growth is colorless and develops no aerial hyphae. No soluble pigment is produced.

(13) On gelatin stab (on 15% plain gelatin incubated at 20° C. or on glucose-peptone-gelatin incubated at 27° C.)

On the plain gelatin medium, the growth is colored pale yellowish brown with developing aerial hyphae of white to pale pink to light gray color. Soluble pigment of brown color is produced.

On the glucose-peptone-gelatin medium, the growth is colored yellowish brown, with developing aerial hyphae of white to light brownish gray color. Soluble pigment of dark brown color is produced.

(14) On skimmed milk (incubated at 37° C.)

The growth is colored pale yellow to pale pink to pale yellowish brown and develops no aerial hyphae. Soluble pigment of pale brown color is produced.

3. Physiological properties (1) Temperature for growth

Growth on starch-yeast extract agar (1.0% soluble starch, 0.2% yeast extract, 3.4% agar, pH 7.0–7.2) was examined at 20° C., 24° C., 27° C., 30° C., 37° C. and 50° C. The MF266-g4 strain grew at all temperatures tested, but not at 50° C. Optimum temperature for good growth appeared to be in the range of 30° C. to 37° C.

(2) Liquefaction of gelatin

Plain gelatin (15%) medium did not start to liquefy when incubated at 20° C. The glucose-peptone-gelatin medium started to liquefy from the 17th day of incubation when incubated at 27° C. The grade of liquefaction was then weak.

(3) Hydrolysis of starch

The starch in the inorganic salts-starch agar medium and in the starch-agar medium started to be hydrolyzed from the 5th day of incubation when incubated at 27° C., and the grade of hydrolysis was medium to strong.

(4) Coagulation and peptonization of skimmed milk

When incubated at 37° C., the skimmed milk did neither coagulate nor peptonize at the end of 21 days incubation.

(5) Formation of melanoid pigment

Pigmentation is observed on tryptone-yeast extract broth (ISP-medium 1), or on peptone-yeast extract iron agar (ISP-medium 6), but not on tyrosine agar (ISP-medium 7), when incubated at 27° C.

(6) Utilization of carbon sources for growth

Utilization of the following carbohydrates was tested in Pridham-Gottlieb agar medium (ISP-medium 9) as incubated at 27° C.

Glucose was utilized for growth. L-Arabinose, D-xylose, sucrose, inositol, raffinose and D-mannitol were not utilized. Utilization of D-fructose and L-rhamnose was doubtful.

(7) Liquefaction of calcium malate

When incubated at 27° C., calcium malate in the calcium malate-agar medium started to be liquefied around the growth at the 7th day of incubation. The grade of liquefaction was medium to strong.

(8) Reduction of nitrate

Reduction of nitrate was positive when tested in an aqueous peptone solution containing 1.0% potassium nitrate (ISP-medium 8) as incubated at 27° C.

Summarizing the above-mentioned properties of the MF266-g4 strain, it is noted that this strain belongs to the genus Streptomyces and is essentially characterized in that its aerial hyphae form open spirals but do not form whirl and that the surface of spore is smooth under microscopic observation. On various culture media, the growth has a color of pale yellow to pale yellowish brown to pink, with developing aerial hyphae of white to pinkish gray to light brownish gray color. The soluble pigment is tinged with yellow to yellowish brown to pale red. Production of melanoid pigment is positive on the tryptone-yeast extract broth medium and on the peptone-yeast extract iron medium, while it is negative on the tyrosine medium. Proteolysis and starch hydrolysis are of medium to strong grade.

On the basis of the above-mentioned characteristics of the MF266-g4 strain, this strain is compared to known analogous species of the genus Streptomyces with reference to descriptions of some publications. It is found that the MF266-g4 strain resembles to and is most closely related to *Streptomyces virginiae* (see reference 1: "Journal of Systematic Bacteriology" 18, 178 (1968), reference 2: Waksman "The actinomycetes" 2, 285) and *Streptomyces lavendulae* (see reference 3: "Journal of Systematic Bacteriology" 18, 138 (1968), reference 4: Waksman "The actinomycetes" 2, 233).

In this situation, we received samples of *Streptomyces virginiae* and *Streptomyces lavendulae* and directly compared them with the MF266-g4 strain. The results of comparison are summarized in Table 3 below.

MF266-g4 strain is of the species related to *Streptomyces virginiae* ISP 5094 and *Streptomyces lavendulae* ISP 5069 and is most related to the former of these known two strains. In consequence, the MF266-g4 strain is identified as *Streptomyces virginiae* MF266-g4.

This Streptomyces MF266-g4 strain has been deposited in the Japanese depository "Fermentation Research Institute, Agency of Industry Science and Technology" since Feb. 6, 1980 under deposit number FERM-P 5401. This MF266-g4 strain has been deposited since June 10, 1981 in the American Type Culture Collection, Washington, D.C., U.S.A. under ATCC number 31910.

Mutation of actinomycetes occurs frequently in either artificial or spontaneous conditions, and accordingly this invention includes the use of the MF266-g4 strain as well as its mutants. In other words, this invention includes the use of all strains of the genus Streptomyces which produce the MF266 substance, as long as they cannot be differentiated evidently from the MF266-g4 strain and its mutants.

The MF266 substance can be obtained by aerobic cultivation of spores or mycelia of an MF266 substance-producing strain of the genus Streptomyces such as Streptomyces MF266-g4 strain. In carrying out the process of this invention, an amount of spores or mycelia of the MF266 substance-producing strain is inoculated to a suitable culture medium therefor comprising nutrient sources and is then incubated under aerobic conditions and preferably submerged aerobic condi-

TABLE 3

| Properties | MF266-g4 strain | Streptomyces virginiae ISP 5094 | Streptomyces lavendulae ISP 5069 |
|---|---|---|---|
| Form of aerial hyphae | Spirals | Spirals (Retinaculiaperti[1]) | Rectiflexibiles or Spirals (Retinaculiaperti[3]) |
| Spore surface | Smooth | Smooth | Smooth (locally with indefinite warty) |
| Color of aerial hyphae | White to pinkish gray to light brownish gray | White to pinkish gray to light brownish gray | White to pinkish gray to light brownish gray |
| Color of growth | Pale yellow to pale yellowish brown or pink | Colorless to pale yellow to pale yellowish brown | Pale yellow to pale yellowish brown or brownish gray |
| Soluble pigment | Yellow to yellowish brown to pale red | Yellow to yellowish brown | Yellow to yellowish brown to brown |
| Production of melanoid pigment | | | |
| On ISP-medium 1: | + | + | + (weak) |
| On ISP-medium 6: | + | + | + |
| On ISP-medium 7: | − | − | + (weak) |
| Hydrolysis of starch | + | + | + |
| Coagulation of milk | − | − | − |
| Peptonization of milk | ∓ | ∓ | + |
| Liquefaction of gelatin | | | |
| In plain gelatin medium | − | − | − |
| In glucose-peptone-gelatin medium | ± | ± | + |
| Reduction of nitrate | + | ± | ∓ (+[4]) |
| Utilization of carbon sources | | | |
| Glucose | + | + | + |
| L-Arabinose | − | − | − |
| D-Xylose | − | − | − |
| D-Fructose | ∓ | − (+[1]) | ∓ |
| Sucrose | − | − | − |
| Inositol | − | − | − |
| L-Rhamnose | ∓ | − | − |
| Raffinose | − | − | − |
| D-Mannitol | − | − | − |

Note:
The symbol "∓" means probable negative.

As will be clear from Table 3, the MF266-g4 strain is well coincident with *Streptomyces virginiae* ISP 5094 in all respects but only except in respect of the reduction of nitrate and utilization of D-fructose and L-rhamnose. While, the MF266-g4 strain is somewhat different from *Streptomyces lavendulae* ISP 5069 in respect of the production of melanoid pigment, peptonization of milk and reduction of nitrate. Accordingly, it is found that the tions, so that there is obtained a culture broth containing the MF266 substance. Generally, constituents of culture media commonly employed for the cultivation of ordinary actinomycetes can be used for the purpose of this invention. For instance, commercially available soybean meal, peanut powder, cotton seed powder, dried yeast, peptone, meat extract, casein, corn steep liquor, N-Z amine, ammonium nitrate, ammonium sulfate, ammonium chloride and the like may be useful as the nitrogen sources. Commercially available carbohydrates such as glucose, starch, glycerol, maltose, dextrin, saccharose, lactose, molasses and the like as well as fat or oil are useful as the carbon source. In addition, sodium chloride, calcium carbonate, magnesium sulfate, manganese chloride, sodium phosphate or other inorganic salts as well as various amino acids can be employed for the salt-additive in the culture medium. Various heavy metal salts may also be added in trace quantities, if required. Any of the nutrient materials which are known for the cultivation of actinomycetes may be employed in the process of this invention, as long as it is assimilable by the MF266 substance-producing strain for the production of the MF266 substance.

For the production of the MF266 substance on large scale, liquid cultivation is preferred. Any temperature at which the MF266 substance-producing strain is able to grow and produce the MF266 substance can be employed for the cultivation, but a preferred cultivation temperature is in the range of 20° to 40° C., especially in a range of 25° to 35° C. The cultivation is continued for a period of time sufficient to produce and accumulate a sufficient amount of the MF266 substance in the culture medium. For instance, a liquid culture medium comprising 2.0% starch, 2.0% soybean meal, 1.0% glucose, 1.0% corn steep liquor, 0.25% ammonium chloride, 0.3% sodium chloride and 0.6% calcium carbonate was prepared and sterilized at pH 6.2–6.4. This liquid medium was then inoculated with spores or mycelia harvested from a slant culture of the MF266-g4 strain. When the inoculated medium was submerged-cultured at 27° C. in a jar-fermentor, the production and accumulation of the MF266 substance in the culture medium reached a maximum at the end of incubation for 2 to 5 days.

Assay of the MF266 substance can be made using *Bacillus subtilis* PCI 219 as the test organism according to a standard cup-plate method which has usually been employed for the assay of known antibiotics. A pure sample of the MF266 substance hydrochloride of this invention which was obtained from Example 3 described later may be used as a standard sample which exhibits a potency of 1000 units per mg. However, upon cultivation of the Streptomyces MF266-g4 strain, there are usually co-produced many of active substances other than the MF266 substance of this invention, and hence in the course of cultivation of the MF266-g4 strain and extraction and purification of the MF266 substance according to this invention, it is difficult to achieve an exact assay of the MF266 substance merely by using the cup-plate method with *Bacillus subtilis* PCI 219. Thus, we have developed a method of assaying the MF266 substance by high-performance liquid chromatography which is conducted under the following conditions of experiment:

Column: a column (6.3 mm inner diameter × 30.5 cm height) of μ-Bondapak C-18 (a product of Waters Co., U.S.A.)

Development solvent: a mixture of methanol-10% aqueous ammonium acetate (3:1 by volume)

Detection: Ultraviolet absorption at 254 nm

Flow rate: 1.0 ml per minute.

When the above liquid chromatographic assay method is conducted under the above-mentioned conditions, the MF266 substance shows a retention time of 8.2 minutes and the assay of the MF266 substance can be achieved by measuring the height of the absorption peak at the retention time of 8.2 minutes.

For recovery of the MF266 substance from the culture medium, it is possible to use various methods such as organic solvent-extraction, adsorption and precipitation, depending on the properties of the MF266 substance. The MF266 substance so recovered may further be purified likewise.

The MF266 substance in its free form is slightly soluble in such organic solvents as chloroform and methanol but hardly soluble in water. On the other hand, the MF266 substance in its acid-addition salt form is soluble in water and methanol but almost insoluble in the other organic solvents. Utilizing solubility of the MF266 substance in various solvents, it is feasible to transfer-extract the MF266 substance from an aqueous solution thereof such as the culture broth, into such water-immiscible organic solvents as chloroform and butanol at a pH of not less than 4. The MF266 substance present in the organic solvents may also be re-transferred into a water phase at a pH of more than 3. On the basis of these properties of the MF266 substance, a countercurrent distribution method is effective for purification of the MF266 substance. For example, the partition coefficient of the MF266 substance in a mixture of chloroform-methanol-sodium acetate buffer solution (2:2:1 by volume) is 0.41 to 0.55 when said buffer solution has pH 3.5; and 0.23 when said buffer solution has pH 4.0. In order to separate the MF266 substance from the accompanying impurities, it is effective to extract the MF266 substance with an organic solvent mentioned above, though the use of the above organic solvent is not suitable for treating a large quantity of the MF266 substance since solubility of the MF266 substance in organic solvent is generally low.

In the culture broth of the MF266 substance-producing strain, the MF266 substance is existing not only in the liquid phase of the broth but also in the mycelium, and therefore it is necessary that the mycelium cake obtained from filtration of the culture broth is extracted effectively to recover the MF266 substance therefrom. To this end, the mycelium cake may be extracted with methanol, aqueous methanol or a weakly acidic methanol for recovery of the MF266 substance. Upon filtration of the culture broth, therefore, it is preferable to preliminarily admix the culture broth with a volume of methanol.

For adsorption of the MF266 substance, various adsorbents may be used, including active carbon as well as a weakly acidic cation-exchange resin such as Amberlite IRC-50 and CG-50 (H-form) (products of Rohm & Haas Co., U.S.A.) and microporous non-ionic adsorbent resin such as Amberlite XAD-2 and XAD-4 and Diaion HP (a product of Mitsubishi Kasei K.K., Japan). The MF266 substance which has been adsorbed by the resinous adsorbent can efficiently be eluted with acidified aqueous acetone or acidified aqueous methanol. Besides, column chromatography with an ion-exchanger such as CM-Sephadex C-25 (a product of Pharmacia Co., Sweden) may be effective for purification of the MF266 substance.

It is also possible to recover the MF266 substance from aqueous solution or mixed aqueous organic solvents according to a conventional precipitation method. For instance, when an acidic aqueous solution of MF266 substance is made neutral or weakly alkaline by addition of an alkali or is admixed with such an organic solvent in which the MF266 substance is insoluble or almost insoluble, the MF266 substance can precipitate and may be recovered by filtration.

The MF266 substance can be recovered in the pure state by effecting the above-mentioned isolation methods and/or purification methods appropriately in combination or with repetition. The MF266 substance in the form of the free base is unstable and hence may preferably be recovered in the form of an acid-addition salt thereof.

The invention is illustrated below with reference to Examples, but this invention is not limited to the following Examples. In view of the properties of the MF266 substance clearly described by this invention, it is feasible to modify the production of the MF266 substance in different ways. Accordingly, this invention includes any modification and variation of the following Examples.

EXAMPLE 1

A loopful quantity of Streptomyces MF266-g4 strain (identified as FERM-P 5401 or ATCC 31910) which was incubated in slant agar medium was inoculated to a sterile liquid culture medium (pH 7.4, 110 ml each in Erlenmeyer flasks of 500-ml capacity) comprising 2.0% glycerol, 2.0% dextrin, 1.0% soybean peptone, 0.3% yeast extract, 0.2% ammonium sulfate and 0.2% calcium carbonate. The inoculated medium was cultured at 27° C. for 48 hours by rotatory shaking (180 r.p.m.) to give a seed culture. The resultant seed culture (220 ml each) was inoculated into two jar-fermentors (30 liters capacity) each containing 15 l. of a liquid culture medium comprising 2.0% starch, 2.0% soybean meal, 1.0% glucose, 1.0% corn steep liquor, 0.25% ammonium chloride, 0.3% sodium chloride and 0.6% calcium carbonate (pH 6.2–6.4). The inoculated medium was cultured at 27° C. for 90 hours under aeration (15 l. air per minute) and with agitation (300 r.p.m.).

The culture broths obtained from the two jar-fermentors were combined together (24 liters) and admixed with 12 l. of methanol, followed by agitating for 1 hour and admixing with a filter aid (diatomaceous earth commercially available under tradename "Hyflo-Supercel", a product of Jones-Manville Sales Corp., U.S.A.). The admixture so obtained was filtered to give 34 l. of the broth filtrate (potency 430 u./ml). The filter cake (mycelium) obtained was admixed with 5 l. of methanol, agitated for 1 hour and filtered. The filtrate obtained was admixed with 10 l. of water and again filtered to afford 15 l. of the filtrate (potency 120 u./ml). This filtrate was combined with the above-mentioned broth filtrate, and the mixture obtained was passed through a column (9×50 cm) of 3 l. of Amberlite XAD-2 resin (a product of Rohm & Haas Co., U.S.A.) for adsorption of the active substance. This resin column was washed with 6 l. of water and then eluted with acetone-0.001 N hydrochloric acid (1:1 by volume). The first running (2.5 l.) from the column was discarded and the next eluate (5.0 l.) was collected as the active fraction (potency 2,790 u./ml).

The active solution (the eluate) was adjusted to pH 6.0 by addition of aqueous sodium hydroxide and then passed through a column (4×40 cm) of 400 ml of Amberlite CG-50 resin (H-form, Type I, a product of Rohm & Haas Co., U.S.A.) for adsorption of the active substance. This resin column was washed with 1.0 l. of methanol-water (3:1 by volume) and then eluted with methanol-0.1 N hydrochloric acid (4:1) to obtain 850 ml of the active eluate. This active solution was adjusted to pH 5.0 by addition of Amberlite IR-45 resin (OH-form) and the resulting mixture was filtered. The filtrate was concentrated to dryness to give 6,300 mg of a red colored crude powder (potency 2,020 u./mg) comprising the MF266 substance hydrochloride.

EXAMPLE 2

The red crude powder (6,300 mg) obtained in the Example 1 above was taken up into 500 ml of water and the aqueous solution was adjusted to pH 6.5 by addition of aqueous sodium hydroxide, followed by extraction three times with 1000 ml-portions of a mixture of chloroform-methanol (9:1 by volume). The combined extract in the organic solvent (totally 2.7 l.) was concentrated to dryness under reduced pressure to give 1,386 mg of a red powder (potency 2,920 u./mg) comprising the MF266 substance hydrochloride.

This red powder (1,380 mg) was subjected to a countercurrent distribution method using a solvent system of chloroform-methanol-0.1 M sodium acetate buffer solution (pH 4.0) (2:2:1) with the volume of the upper and lower layers being each 10 ml. After 79 transfers, the lower and upper phases of the tube Nos. 9–26 were collected together and concentrated to 110 ml under reduced pressure. The concentrated solution was adjusted to pH 7.4 by addition of aqueous sodium hydroxide and then extracted with 500 ml of a mixture of chloroform-methanol (9:1). The solvent extract was concentrated to dryness under reduced pressure to give 588 mg of a red powder (potency 2,140 u./mg).

The red powder (580 mg) so obtained was again likewise subjected to the countercurrent distribution method using a solvent mixture of chloroform-methanol-0.1 M sodium acetate buffer solution (pH 3.5) (2:2:1 by volume). After 79 transfers, the upper and lower phases of the tube Nos. 20–34 were collected together and the combined solution was distilled to remove the organic solvents therefrom. The concentrated aqueous solution obtained was adjusted to pH 7.4 by addition of aqueous ammonia and then extracted with 500 ml of chloroform-methanol (9:1), and the organic solvent extract was concentrated to dryness under reduced pressure to give 195 mg of a red powder (potency 1,837 u./mg).

This red powder was further subjected to the countercurrent distribution method in the same way as mentioned above using the same solvent system. After 99 transfers, the upper and lower phases of the tube Nos. 31–40 were collected together and subsequently processed in the same manner as above to afford 85.5 mg of a red powder (potency 1,337 u./mg) comprising the MF266 substance. When this red powder was assayed by the high-performance liquid chromatography as described hereinbefore, it showed a purity of about 65%.

EXAMPLE 3

The red powder obtained in the Example 2 above was subjected to the high-performance liquid chromatography which was conducted under the following conditions, and the fraction which exhibited a peak at the retention time of 22 to 29 minutes was collected.

Column: μ-Bondapak C-18 (a product of Waters Co., U.S.A.), Inner diameter: 9.5 mm, Height: 30.5 cm Eluent: Methanol-10% aqueous ammonium acetate (3:1 by volume)

Detection: Ulraviolet absorption at 280 nm and refractive index.

Sample feed: A solution of 10 mg/ml of the sample in methanol-10% aqueous ammonium acetate (3:1 by volume) was charged at a rate of 0.5 ml for each injection.

The fraction collected (220 ml) was admixed with 500 ml of water and further with 900 ml of chloroform, and the resulting admixture was adjusted to pH 7.4 by addition of aqueous ammonia. The admixture was well agitated to extract the MF266 substance into the chloroform phase. The extract in chloroform was washed twice with 500 ml-portions of water, dried over anhydrous sodium sulfate and then concentrated to dryness in vacuo to give 31 mg of a red powder. This red powder was taken up into 50 ml of 0.001 N hydrochloric acid and the solution was freeze-dried to afford 31 mg of a red powder of the MF266 hydrochloride which showed a potency of 1,000 u./mg.

What we claim is:

1. The MF266 substance which is a red colored amphoteric compound and of which the hydrochloride decomposes at 178°–180° C. and shows a specific optical rotation $[\alpha]_D^{25} = +370°$ (c 0.1, methanol) and an elemental analysis: C 49.00%, H 6.56%, N 3.39%, O 28.58%, Cl 7.17%, the infrared absorption spectrum of the MF266 substance hydrochloride pelleted in potassium bromide giving main absorption peaks as shown in FIG. 1 of the attached drawings, and the ultraviolet absorption spectra of the MF266 substance hydrochloride giving absorption maxima at 220, 235, 254, 290, 380, 475, 496, 535 and 575 nm with $E_{1\ cm}^{1\%}$ values of 208, 276, 232, 64, 28, 96, 100, 64 and 14, respectively when determined in methanol; absorption maxima at 220 (shoulder), 235, 254, 290, 380, 480, 497, 535 and 570 nm with $E_{1\ cm}^{1\%}$ values of 188, 264, 241, 64, 28, 92, 100, 60 and 14, respectively when determined in 0.1 N hydrogen chloride in 90% aqueous methanol; and absorption maxima at 213, 253, 292, 360, 560 and 597 nm with $E_{1\ cm}^{1\%}$ values of 688, 247, 48, 36, 100 and 100, respectively when determined in solution in 0.1 N aqueous sodium hydroxide in 90% aqueous methanol as shown in FIG. 2 of the attached drawings, the MF266 substance hydrochloride being further characterized by that it is soluble in water, methanol, dimethylsulfoxide and pyridine but sparingly soluble in chloroform, acetone, benzene and ethyl acetate and that it gives a single spot at Rf 0.27 in a thin layer chromatography on silica gel developed with chloroform-methanol-10% aqueous ammonium acetate (20:15:1 by volume) and a single spot at Rf 0.06 in the same silica gel thin layer chromatography developed with chloroform-methanol (1:1 by volume) and a single spot at Rf 0.10 in the same silica gel thin layer chromatography developed with chloroform-methanol-acetic acid (20:5:1 by volume) as eluent.

2. A pharmaceutically acceptable acid addition salt of the MF266 substance as defined in claim 1.

3. A process for the production of the MF266 substance as defined in claim 1, which comprises cultivating Streptomyces MF266-g4 strain (FERM-P 5401; ATCC 31910) under aerobic conditions in a culture medium containing assimilable carbon and nitrogen sources to produce and accumulate the MF266 substance in the culture, and recovering the MF266 substance from the culture.

4. The process as claimed in claim 3 in which the cultivation is carried out at a temperature of 25° to 35° C. for 2 to 5 days.

5. A pharmaceutical composition, useful as an antibacterial agent or as an antitumor agent in the treatment of L-1210 leukemia in mice, comprising as the active ingredient the MF266 substance as defined in claim 1 or a pharmaceutically acceptable salt thereof in an amount effective to inhibit the growth of bacteria or mouse L-1210 leukemia tumor cells, in combination with a carrier for the active ingredient.

* * * * *